US00PP10781P

United States Patent [19]

Wolf et al.

[11] Patent Number: Plant 10,781

[45] Date of Patent: Feb. 9, 1999

[54] HEATHER PLANT NAMED 'ANETTE'

[75] Inventors: Paul Wolf; Werner Wolf, both of Seligenstadt, Germany

[73] Assignee: Kurt Kramer, Edewecht, Germany

[21] Appl. No.: 923,732

[22] Filed: Sep. 4, 1997

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 9,710 11/1996 Kramer ..... Plt./54.1

P.P. 9,789 1/1997 Kramer ..... Plt./54.1

*Primary Examiner*—Howard J. Locker

*Assistant Examiner*—Kent L. Bell

*Attorney, Agent, or Firm*—C. A. Whealy

[57] ABSTRACT

A distinct cultivar of Heather plant named 'Anette', characterized by its bright pink flower buds that maintain color throughout the winter; light green leaf color without reddish tones; and freely and strong basal branching habit.

2 Drawing Sheets

The present invention relates to a new and distinct cultivar of Heather plant, botanically known as *Calluna vulgaris,* and hereinafter referred to by the cultivar name 'Anette'.

The new Heather was discovered by the inventors in Seligenstadt, Germany, in July, 1992, as a naturally-occurring mutation of the *Calluna vulgaris* cultivar 'Melanie' (U.S. Plant Pat. No. 9,789). The new Heather was observed as a single plant with pink-colored flower buds in a group of plants of the parent cultivar which has white-colored flower buds.

Asexual reproduction of the new Heather by terminal cuttings taken at Edewecht, Germany, has shown that the unique features of this new Heather are stable and reproduced true to type in successive generations.

The following traits have been repeatedly observed and are determined to be the unique characteristics of 'Anette'. These characteristics in combination distinguish 'Anette' as a new and distinct cultivar:

1. Bright pink flower buds that maintain color throughout the winter.
2. Light green leaf color without reddish tones.
3. Freely and strong basal branching.

The new Heather has not been observed under all possible environmental conditions. The phenotype may vary somewhat with variations in environment such as temperature and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The first photograph comprises a top perspective view of a typical plant of 'Anette'.

The second photograph comprises a close-up view of mature flower buds. The flower and foliage colors in these photographs appear different than the actual colors due to light reflectance.

DETAILED BOTANICAL DESCRIPTION

In the following description, color references are made to The Royal Horticultural Society Colour Chart except where general terms of ordinary dictionary significance are used.

The following observations and measurements describe plants grown in Edewecht, Germany, under commercial field conditions.

Botanical classification: *Calluna vulgaris* cultivar 'Anette'.

Commercial classification: Broom Heather.

Parentage: Naturally-occurring mutation of the *Calluna vulgaris* cultivar 'Melanie' (U.S. Plant Pat. No. 9,789).

Propagation:

*Type.*—Terminal cuttings.

*Time to rooting.*—About 30 and 40 days with soil temperatures of 25 and 18°C, respectively.

*Rooting habit.*—Fibrous and freely branching.

Plant description:

*Appearance.*—Generally low mounded shrub, freely and strong basal branching, very dense. Flower spikes arise at terminal apices. Numerous axillary branches below flower spikes. Appropriate for 500-ml to 3-liter containers.

*Plant height from soil level to top plant plane.*—About 16 cm.

*Growth rate.*—Moderate to rapid.

*Vigor.*—Moderate to high.

*Crop time.*—About 14 months are required from unrooted cuttings to finishing in a 10 to 15-cm container. Plants are generally grown without supplemental heat and pruned twice during production.

*Foliage description.*—Opposite, scale-like and bractiolate, sessile, arranged on stems which are roughly square in cross-section. Length: 1 to 2 mm. Width: 0.3 to 0.8 mm. Color: Mature foliage, 146B.

Flower description:

*Appearance.*—Flowers formed at the terminals of main branches. Flower spikes have numeruous uniformly-spaced auxiliary verticils with clusters of 2 to 4, or more, mature buds outwardly radiating from the apex of oppositely-placed, short branches arising from leaf axils. Length of spikes is normally about 10 cm. The number of buds formed is about average for the species. Flower buds do not open to a flower, but rather remain in the bud stage. The corolla characteristics and the reproductive organs of the new Heather are typical of the species. Flowering recurrent.

*Natural flowering season.*—The new Heather produces flower buds in the fall (September through November) and remain in the bud stage for about 6 months, or until early spring.

*Flower bud description.*—Shape: Elliptic. Length: About 5 mm. Diameter: 1 to 2 mm. Sepal color: 64C, fading to light pink to white.

Disease resistance: No known resistance to Heather diseases has been observed to date on plants grown under commercial conditions. Infection with *Glomorella cingulata* and *Botrytis cinerea* is possible.

Seed production: The new Heather does not produce seed because the pistil is covered by the calyx.

It is claimed:

1. A new and distinct cultivar of Heather plant named 'Anette', as illustrated and described.

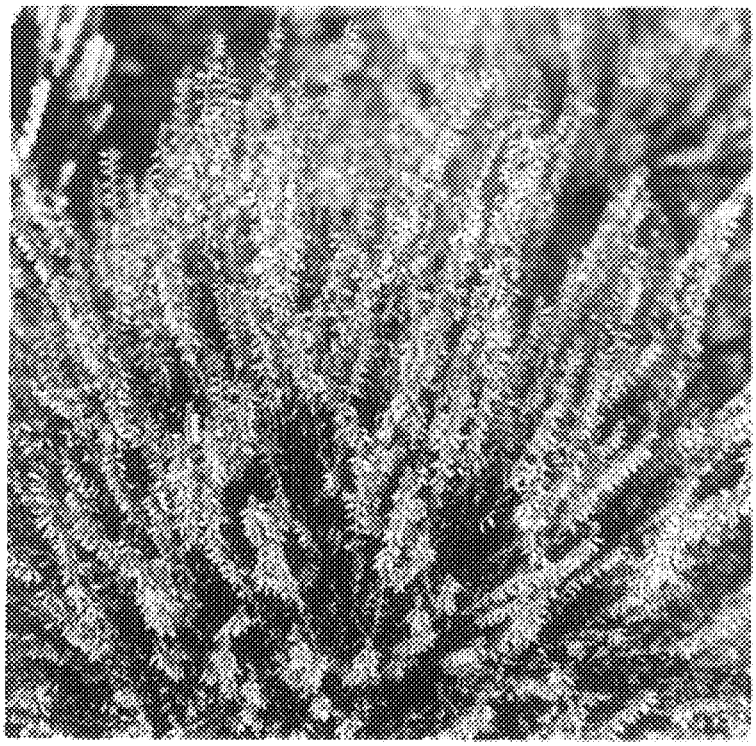

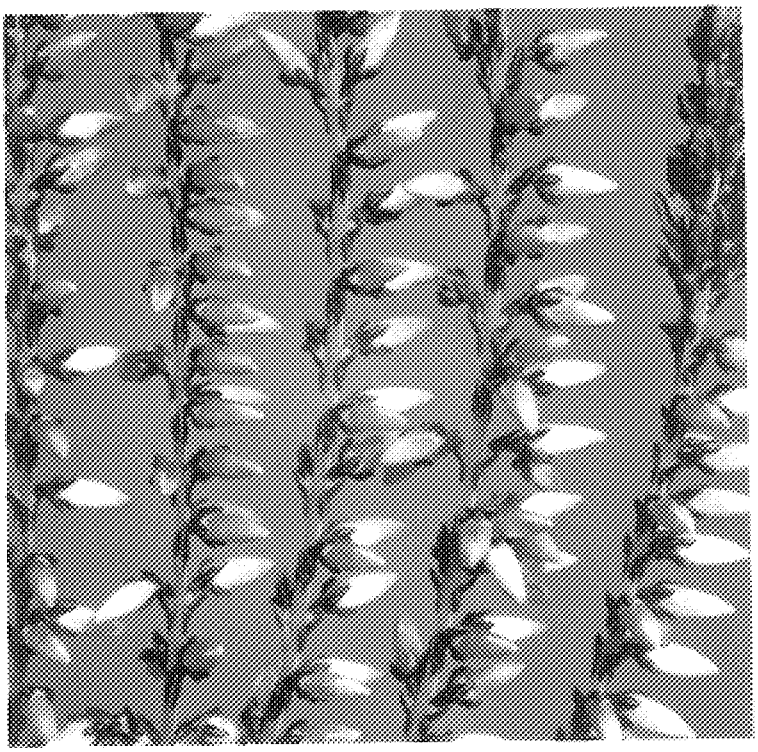

* * * * *